United States Patent [19]

De Lange

[11] Patent Number: 5,098,401

[45] Date of Patent: Mar. 24, 1992

[54] DISPOSABLE AUTOMATIC NEEDLE COVER ASSEMBLY WITH SAFETY LOCK

[76] Inventor: Andries G. De Lange, 4141 Rosemeade Pkwy. #7202, Dallas, Tex. 75287

[21] Appl. No.: 637,616

[22] Filed: Jan. 4, 1991

[51] Int. Cl.[5] .................................. A61M 5/32
[52] U.S. Cl. ..................................... 604/192; 604/198
[58] Field of Search ............... 604/110, 162, 167, 192, 604/198, 263

[56] References Cited

U.S. PATENT DOCUMENTS

| | | | |
|---|---|---|---|
| 3,134,380 | 5/1964 | Armao | 604/198 |
| 4,139,009 | 2/1979 | Alvarez | 604/198 |
| 4,735,618 | 4/1988 | Hagen | 604/192 |
| 4,795,432 | 1/1989 | Karczmer | 604/263 |
| 4,846,809 | 7/1989 | Sims | 604/263 |
| 4,911,694 | 3/1990 | Dolan | 604/110 |
| 4,915,697 | 4/1990 | DuPont | 604/192 |
| 4,917,672 | 4/1990 | Terndrup et al. | 604/263 |
| 4,955,866 | 9/1990 | Corey | 604/192 |

FOREIGN PATENT DOCUMENTS

| | | | |
|---|---|---|---|
| 3808688 | 1/1989 | Fed. Rep. of Germany | 604/263 |
| 3802353 | 8/1989 | Fed. Rep. of Germany | 604/192 |
| 2208604 | 4/1989 | United Kingdom | 604/192 |

*Primary Examiner*—C. Fred Rosenbaum
*Assistant Examiner*—Sharon Finkel

[57] ABSTRACT

A needle assembly and flexible automatic needle cover, with a safety lock which can be used with any conventional hypodermic syringe. The needle assembly has an off-centered conical end. The automatic needle cover is fixed to the off-centered conical end and is flexible. The automatic needle cover has evenly spaced incisions along part of its length, and a groove around the bottom. The bottom part of the automatic needle cover is solid except for an off-centered orifice. Fitting over the front of the automatic needle cover is the safety lock with an off-centered orifice during use. The safety lock can be rotated around the automatic needle cover to close the needle after use.

1 Claim, 3 Drawing Sheets

DISPOSABLE AUTOMATIC NEEDLE COVER ASSEMBLY WITH SAFETY LOCK

BACKGROUND OF THE INVENTION

This invention relates to disposable hypodermic syringes and in particular to an automatic needle cover assembly with a safety lock, which will protect all concerned individuals while using the device.

The disposable needles that are available at the moment do not supply adequate protection to the person administering the injection. There is always the danger of pricking oneself while the cover of the needle is being replaced and in some cases the cover does not even get replaced, the needle is then left exposed. This exposes people who must dispose of the used needle to the danger of getting pricked by a needle which could possibly be carrying an infectious disease.

This invention's purpose is to overcome the above-mentioned drawbacks, in the manner set forth in the detailed description of the preferred embodiment.

SUMMARY OF THE INVENTION

The main objective of this invention is to provide a disposable automatic needle cover assembly with a safety lock which will eliminate the danger of exposed needles before and after usage.

Another objective of this invention is to provide a disposable automatic needle cover assembly with a safety lock which can be used with any hypodermic syringe.

DETAILED DESCRIPTION OF THE PREFERRED EMBODIMENT

Figure 1:
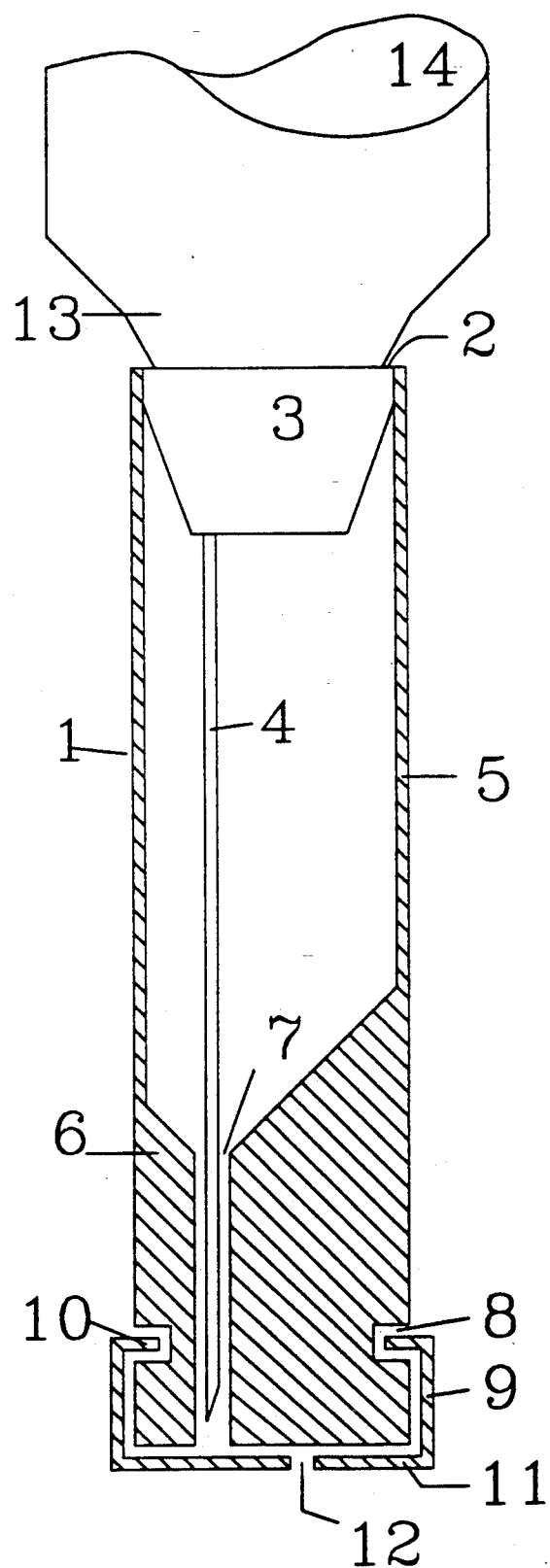
FIG. 1 is an elevational view of the disposable automatic needle cover assembly with safety lock before usage thereof, and with the safety lock closed.
Figure 2:
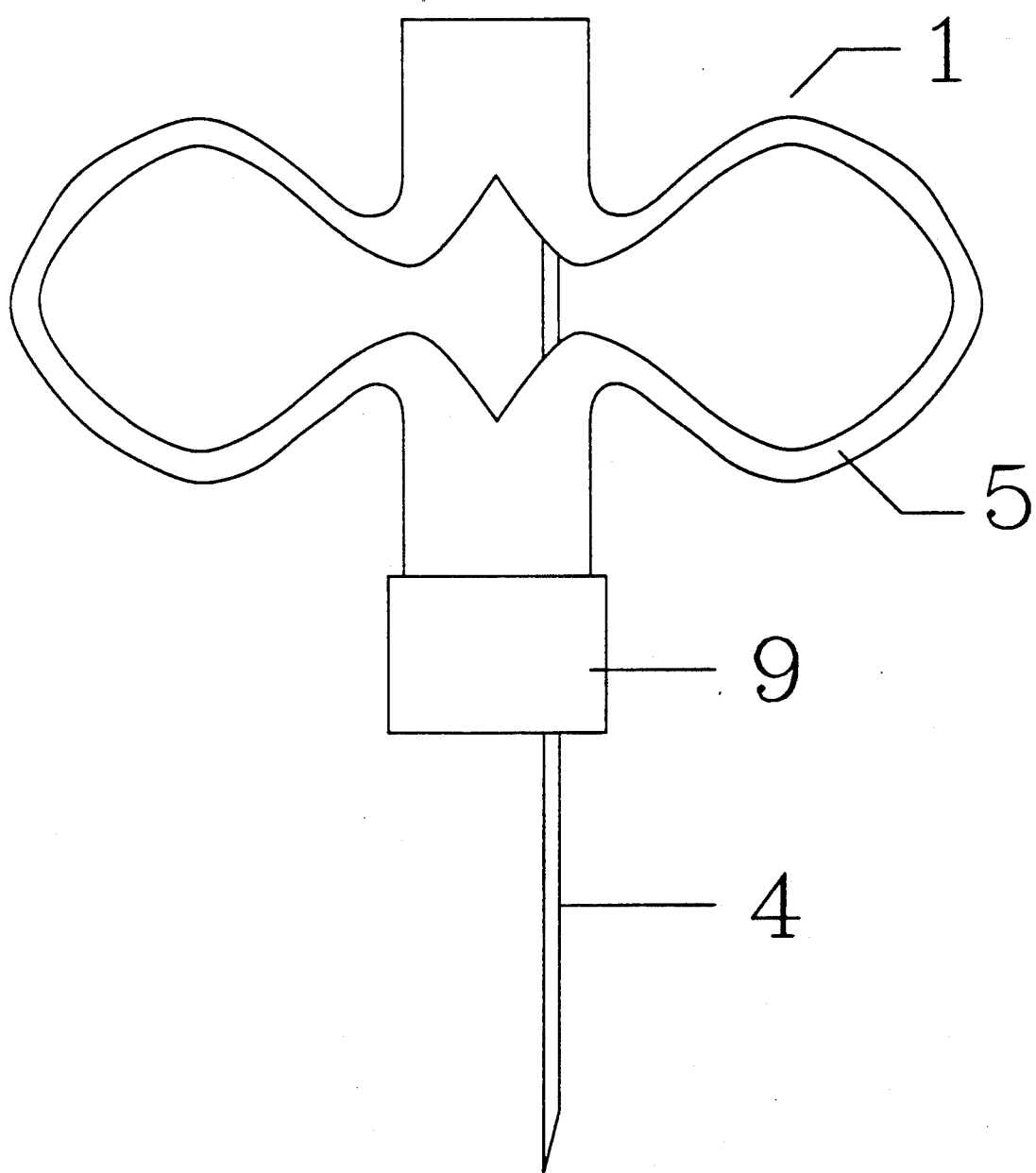
FIG. 2 is an elevational view of the disposable automatic needle cover assembly with safety lock, with the safety lock open and the automatic needle cover retracted.
Figure 3:
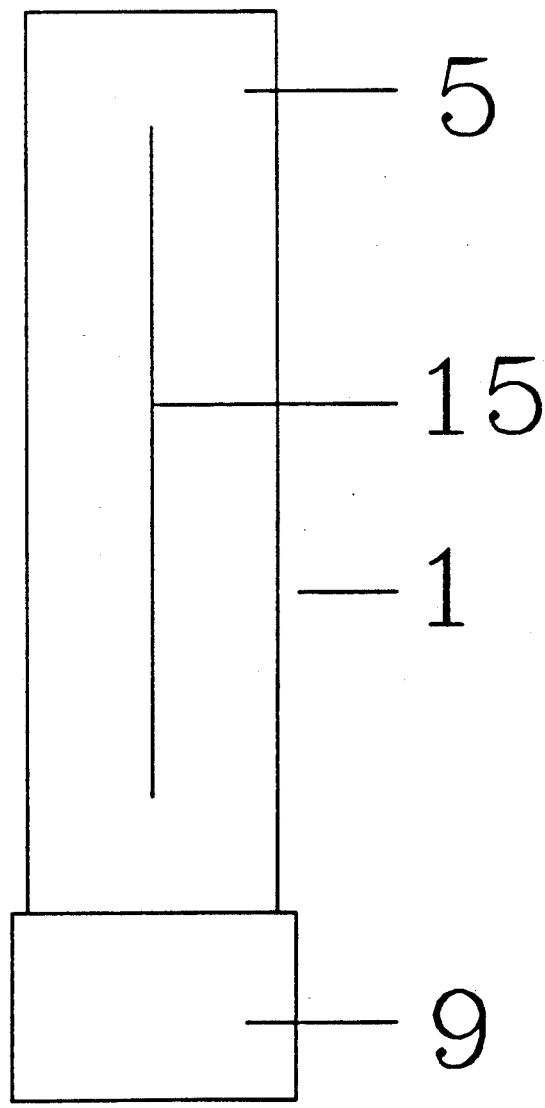
FIG. 3 is an elevational view of the disposable automatic needle cover only, showing the length and position of the incisions.

Referring to FIGS. 1-3 it can be seen that the present invention comprises a disposable automatic needle cover assembly 1 and a safety lock 9 for use in conjunction with any standard hypodermic syringe 14.

The automatic needle cover 5 is made to be retractable and covers the needle 4 completely. The automatic needle cover 5 is attached at the top of the off-centered conical end 3. The automatic needle cover 5 itself is moulded from a flexible material such as rubber and it is moulded in the form of a tube with the front closed in to form a solid front 6 except for the off-centered orifice 7 to facilitate the passing through of the needle 4 during use. Around the outside of the solid front 6 there is a groove 8 to allow the safety lock 9 to be attached to the automatic needle cover 5. Along the length of the automatic needle cover there are two or more incisions 15 to make for easier and further retraction during use. These incisions 15 start below the point where the automatic needle cover 5 is attached to the off-centered conical end 3 and they end at the beginning of the solid end 6. The incisions 15 are spaced evenly around the automatic needle cover 5. (See FIG. 3)

The safety lock 9 is made from a hard material that would not allow the needle to penetrate it. The safety lock 9 is shaped like a cap with a lip 10 around the open side to fit into the groove 8 of the automatic needle cover 5. In the closed end 11 of the safety lock 9 there is an off-centered orifice 7 only when the safety lock 9 is rotated to the open position to allow the needle 4 to pass through during use.

Referring to drawing No. 2 it can be seen how the automatic needle cover 5 retracts during use. The automatic needle cover 5 will return to its original position automatically after use. The safety lock 9 is then rotated to the closed position, and the needle cannot be exposed. This would allow the disposable automatic needle cover assembly lock to be removed from the syringe 14 in a safe manner, and then it could be disposed of in the normal way.

I claim:

1. A disposable automatic needle cover assembly with safety lock for use in combination with a syringe having a body, a plunger, a tapered nozzle, and a needle; the body of the syringe being hollow and open at the back to facilitate the insertion of the plunger into the body of the syringe; the front of the body being shaped to form a tapered nozzle for the frictional attachment of a needle, the plunger fitting snugly into the hollow body of the syring and sliding into and out of the body; said needle being hollow and having an off-centered conical end; wherein said automatic needle cover comprises a cylindrical sheath completely covering the needle and having an inwardly tapering off-centered orifice, said automatic needle cover being made from a flexible material enabling it to be retractable and able to return to its original shape after retraction, said cover having incisions along the length of said automatic needle cover starting below the portion to be attached to the off-centered conical, end and ending at a solid end of said automatic needle cover; said incisions being spaced evenly around said automatic needle cover; said automatic needle cover being solid at the front except for an off-centered orifice to allow the needle to pass through; said solid end of said automatic needle cover having a groove around the outside to allow the safety lock to be attached to said automatic needle cover securely and to allow said safety lock to be rotated around said automatic needle cover; said safety lock being shaped to fit over the solid end of said automatic needle cover like a cap, with the one end being completely open save for a lip to fit into the groove in the solid end of said automatic needle cover; the other end of said safety lock being closed except for an off-centered opening which lines up with said off-centered orifice in said solid end of said automatic needle cover; whereby said safety lock can be rotated around said automatic needle cover to line the off-centered opening up with the off-centered orifice in the automatic needle cover to allow the needle to pass through during use and also be rotated to a closed position to lock the needle safely within said automatic needle cover.

* * * * *